United States Patent
Huang et al.

(10) Patent No.: US 11,318,154 B2
(45) Date of Patent: May 3, 2022

(54) **METHOD OF TREATING *CLOSTRIDIUM DIFFICILE* INFECTION OR ITS ASSOCIATED SYMPTOMS**

(71) Applicants: City University of Hong Kong, Kowloon (HK); Cornell University, Ithaca, NY (US)

(72) Inventors: Linfeng Huang, Shatin (HK); Yung-fu Chang, Ithaca, NY (US); Yingxue Li, Kowloon Tong (HK); Yutian Ren, Kowloon Tong (HK); Wei Xu, Kowloon Tong (HK)

(73) Assignees: City University of Hong Kong, Kowloon (HK); Cornell University, Ithaca, NY (US)

( * ) Notice: Subject to any disclaimer, the term of this patent is extended or adjusted under 35 U.S.C. 154(b) by 99 days.

(21) Appl. No.: 16/541,331

(22) Filed: Aug. 15, 2019

(65) Prior Publication Data
US 2021/0046099 A1 Feb. 18, 2021

(51) Int. Cl.
*A61K 31/704* (2006.01)
*A61P 31/04* (2006.01)
*C12N 15/113* (2010.01)

(52) U.S. Cl.
CPC ............ *A61K 31/704* (2013.01); *A61P 31/04* (2018.01); *C12N 15/113* (2013.01); *C12N 15/1136* (2013.01); *C12N 2310/14* (2013.01)

(58) Field of Classification Search
None
See application file for complete search history.

(56) References Cited

FOREIGN PATENT DOCUMENTS

CN 108486108 * 9/2018 ............. C07K 14/47

OTHER PUBLICATIONS

Liu et al., "High mobility group box1 protein is involved in acute inflammation induced by Clostridium difficile toxin A" Acta Biochim Biophys Sin vol. 48 No. 6 pp. 554-562 doi: 10.1093/abbs/gmw038 (Year: 2016).*
Gu et al., "High-mobility group box 1 protein contributes to the immunogenicity of rTcdB-treated CT26 cells" Acta Biochim Biophys Sin vol. 50 No. 9 pp. 921-928 doi: 10.1093/abbs/gmy078 (Year: 2018).*
Merriam-Webster's Collegiate Dictionary, Tenth Edition, Published 1998 by Merriam-Webster, Inc, p. 924 (Year: 1998).*
Leffler et al., "Clostridium difficile Infection" The New England Journal of Medicine vol. 372 pp. 1539-1548 DOI: 10.1056/NEJMra1403772 (Year: 2015).*
English machine translation of CN108486108, downloaded from https://worldwide.espacenet.com (Year: 2018).*
Kurreck, J., "Antisense technologies: Improvement through novel chemical modifications" Eur J Biochem vol. 270 pp. 1628-1644 doi:10.1046/j.1432-1033.2003.03555.x (Year: 2003).*

* cited by examiner

*Primary Examiner* — Eric Olson
(74) *Attorney, Agent, or Firm* — Renner Kenner Greive Bobak Taylor & Weber

(57) ABSTRACT

A method of preventing or treating a subject suffering from *Clostiridium difficile* infection or its associated symptom includes administering a therapeutic effective amount of a HMGB1 inhibitor to the subject. A method of inhibiting toxin-induced cytotoxic effect in colon cells includes contacting the colon cells with an effective amount of a HMGB1 inhibitor.

5 Claims, 17 Drawing Sheets

Specification includes a Sequence Listing.

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Synthesized

<400> SEQUENCE: 1
ggcccguuau gaaagagaau u                                              21

<210> SEQ ID NO 2
<211> LENGTH: 21
<212> TYPE: RNA
<213> ORGANISM: Artificial Sequence
<220> FEATURE:
<223> OTHER INFORMATION: Synthesized

<400> SEQUENCE: 2
ccucuucugc ucugaguauu u                                              21
```

METHOD OF TREATING *CLOSTRIDIUM DIFFICILE* INFECTION OR ITS ASSOCIATED SYMPTOMS

SEQUENCE LISTING

The Sequence Listing file entitled "sequencelisting" having a size of 613 bytes and a creation date of Aug. 15, 2019, that was filed with the patent application is incorporated herein by reference in its entirety.

TECHNICAL FIELD

The present invention relates to a method of treating *Clostiridium difficile* infection or its associated symptoms, particularly but not exclusively relates to a method of treating *C. difficile* infection induced by toxins.

BACKGROUND OF THE INVENTION

*C. difficile* infection (CDI) is a rapidly emerging life-threatening disease. It's the leading cause of antibiotic-associated intestinal disease. Antibiotic-mediated suppression of normal gut microbiota is strongly associated with colonization and proliferation of *C. difficile* (Rupnik et al., 2009). The clinical outcomes can range from asymptomatic carrier status to diarrhea and (potentially fatal) pseudomembranous colitis. *C. difficile* infection is mainly mediated by toxins such as toxin A (TcdA) and toxin B (TcdB). The emergence of high virulence strains *C. difficile* BI/NAP1/027 poses a significant threat to public health (Loo et al., 2005; O'Connor et al., 2009). Incidence and mortality rates have been rising globally over the past decades. In 2011, roughly half a million infections and 29,000 death were caused by *C. difficile* in the U.S. (Lessa et al., 2015). Patients suffering from *C. difficile* infection are generally subject to antibiotic treatment. However, the prolonged or frequent administration of the antibiotics could substantially disrupt the normal intestinal flora and the patients may become more susceptible to *C. difficile*, resulting in high recurrent rate.

Therefore, *C. difficile* infection is global healthcare problem with limited effective treatment options. There remains a strong need for novel compounds which are useful in the treatment of *C. difficile* infection.

SUMMARY OF THE INVENTION

In a first aspect, the present invention pertains to a method of preventing or treating a subject suffering from *Clostiridium difficile* infection or its associated symptom, comprising administering a therapeutic effective amount of a HMGB1 inhibitor to the subject.

In an embodiment, the *C. difficile* infection or its associates symptom is induced by *C. difficile* toxin B.

In an embodiment, the HMGB1 inhibitor is a chemical compound or a small RNA molecule targeting HMGB1. Preferably, the HMGB1 inhibitor is glycyrrhizin or its derivative.

Particularly, the HMGB1 inhibitor is administered to the subject by a route selected from a group consisting of oral delivery, intravenous delivery, intradermal delivery, intraperitoneal delivery and intramuscular delivery.

In an embodiment, the HMGB1 inhibitor delays or inhibits the onset of TcdB induced tissue damage in the subject.

In an embodiment, the subject has a reduced expression of CCL2 before administering the HMGB1 inhibitor compared to a healthy individual.

In a second aspect, the present invention also pertains to a method of inhibiting toxin-induced cytotoxic effect in colon cells, comprising the step of contacting the colon cells with an effective amount of a HMGB1 inhibitor.

In a third aspect, the present invention relates to use of a HMGB1 inhibitor in the treatment of *C. difficile* infection or its associated symptom, particularly *C. difficile* infection or its associated symptom induced by toxin B.

In a further aspect, the present invention relates to use of a HMGB1 inhibitor in the preparation of a medicament for treating *C. difficile* infection or its associated symptom.

The inventors unexpectedly found that HMGB1 plays an important role in *C. difficile* infection particularly *C. difficile* toxin B induced infection. The inventors also found that inhibition of HMGB1 can help to delay the onset of TcdB induced cell damages or cell death, and protect the intestinal tissues from apoptosis for example by decreasing caspase activation and enhancing cell rounding resistance. Glycyrrhizin which is known to be HMGB1 inhibitor has been demonstrated to be effective against TcdB induced cell death and capable of protecting the colon cells from TcdB. Accordingly, the present invention provides an effective and alternative approach in treating and/or preventing *C. difficile* infection.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 1A is a chromatographic pattern of purified recombinant TcdB on a SDS-PAGE gel, wherein the TcdB was obtained from transfected cells; M refers to the protein marker.

FIG. 1B shows cell viability and caspase 3/7 activity of Caco-2 cells treated with various concentrations of TcdB (0, 0.01, 0.1, 1 or 5 nM) at 18 h post-intoxication.

FIG. 1C is a Western blot pattern of PARP cleavage for cell lysates treated with TcdB, wherein GAPDH was used as a loading control and Staurosporine (STS) was used as the positive control.

FIG. 1D shows the mRNA expression of UGP2 and p22phox in Caco-2 cells transfected with the respective siRNA for knockdown so as to confirm siRNAs useful for acting as positive control, in which qRT-PCR experiment was performed.

FIG. 1E is a plot showing caspase 3/7 activity of Caco-2 cells transfected with siRNA (si-p22phox and si-UGP2) and then treated with indicated amount of TcdB (0, 0.001, 0.01, 0.1, 1 or 5 nM), in which the caspase 3/7 activity was measured by Caspase Glo 3/7 assay at 18 h post-intoxication, and siNC: siRNA acts as the negative control. Data are from three independent replicates.

FIG. 2A is a schematic diagram showing two rounds of pro-siRNA screen and validation for host factors of TcdB.

FIG. 2B is a plot showing the distribution of caspase 3/7 activity relative values for all 1,920 pro-siRNAs.

FIG. 2C shows Z-score calculated based on the results in FIG. 2B.

FIGS. 2D and 2E show the relative caspase 3/7 activity and cell viability of transfected cells after knocking down candidate genes using synthetic siRNA and TcdB intoxication. The candidate gens include HMGB1, AHNAK, OGFR, SSRP, JUP, ITGB1 and SLK. Data were collected from three independent replicates.

FIGS. 3A, 3B and 3C show caspase activity and cell viability of Caco-2 cells after pre-treatment of glycyrrhizin (denoted as gly in the plot), compound glycyrrhizin injection (denoted as CGI), or Magnesium Isoglycyrrhizinate Injection (denoted as MII) and after intoxication with TcdB at different concentrations. Data were collected from three independent replicates.

FIG. 4A shows microscopic images of colonic tissues obtained from mice that received pre-treatment of CGI for 2 days before TcdB injection into the segments and corresponding histological score, wherein the left-top image refers to the control group using a control buffer and saline, the right-top image refers to the control group using a control buffer and TcdB, the left-bottom image refers to the treatment group treated with 50 mg/kg glycyrrhizin and TcdB and the right-bottom image refers to the treatment group treated with 100 mg/kg glycyrrhizin and TcdB.

DETAILED DESCRIPTION OF THE INVENTION

Figure 1A:
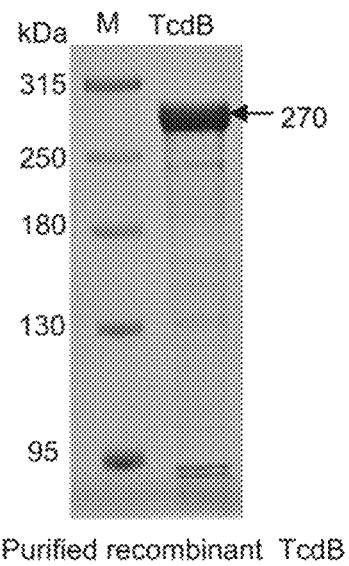

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in the first aspect provides a method of treating a subject suffering from *Clostiridium difficile* infection or its associated symptom. *C. difficile* infection is an intestinal disease caused by toxins produced by the spore forming bacterium *Clostiridium difficile*. *C. difficile* infection is usually correlated with an antibiotic-medicated suppression of normal gut microbiota, which allows abnormal growth and proliferation of *C. difficile* in the gut and thus results in symptoms such as diarrhoea, fever, loss of appetite, nausea, abdominal pain, etc. Severe inflammation may be triggered and cause pseudomembranous colitis which can be fatal. It would be appreciated that diagnosis of such an infection can be done by testing faeces from a subject suffering from diarrhoea, or other suitable tests known in the art.

There are two toxins generally produced by the bacterium causing the disease, i.e. toxin A and toxin B. In an embodiment of the present invention, the *C. difficile* infection or its associated symptoms as described above is induced by toxin B (TcdB). TcdB is a cytotoxin which can lead to rapid change in cell morphology and cell signalling, and thereby causing cell death for example via inducing apoptosis or decreasing integrity of cytoskeleton actin filament. In an embodiment herein, the method of the present invention aims to prevent or treat TcdB induced *C. difficile* infection or its associated symptom.

"Treating" *C. difficile* infection or its associated symptom in particular includes delaying or inhibiting the onset of *C. difficile* infection or its associated symptom, inhibiting the colonization, proliferation and/or growth of the bacterium *C. difficile* in the subject, reducing cell death in the infected intestinal tissues, alleviating symptoms associated with the infection. As described above, the associated symptoms include diarrhoea, fever, loss of appetite, nausea, abdominal pain or combinations thereof.

In an embodiment, the method can be used as a precautionary method to prevent a subject from suffering *C. difficile* infection or its associated symptom as the method is capable of boosting the immune system, keeping the integrity of the intestinal tissues, and/or minimizing the undesired effect caused by antibiotics on the normal intestinal flora in a subject who is susceptible to *C. difficile* infection.

The method of the present invention comprises a step of administering a therapeutic effective amount of a HMGB1 inhibitor to the subject. The HMGB1 inhibitor refers to any compounds or molecules that are capable of inhibiting the expression of HMGB1. Preferably, the HMGB1 inhibitor for the invention is a chemical compound or a small RNA molecule targeting the HMGB1. The chemical compound may be a synthesized compound or a naturally occurring compound. In an embodiment, the compound may be glycyrrhizin or its derivative. Glycyrrhizin, also being known as glycyrrhizic acid, has not been reported to be useful in treating *C. difficile* infection or TcdB induced *C. difficile* infection. Glycyrrhizin was identified to be a HMGB1 inhibitor by binding directly to both HMG boxes in HMGB1 and suppressing chemoattractant and mitogenic activities of HMGB1 (Mollica et al., 2007). The inventors through the experiments have proven that glycyrrhizin has a protective effect against *C. difficile* infection. It would be appreciated that the use of this compound may be useful to minimize undesired effects that are generally caused by the antibiotics and cause less harm to the normal intestinal flora.

In another embodiment, additional compounds including, but are not limited to, nicotine, (−)-epigallocatechin gallate (EGCG), tanshinone, chlorogenic acid, emodin-6-O-β-D-glucoside, rosmarinic acid, isorhamnetin-3-O-galactoside, persicarin, forsythoside B, chloroquine, acteroside, shikonin, and a derivative thereof, may also be used in the present invention. These compounds are found to have inhibitory effect on endotoxin-induced HMGB1 secretion. Any of these compounds may be administered in combination with glycyrrhizin or its derivative to treat *C. difficile* infection or its associated symptoms, particularly *C. difficile* infection induced by toxin B.

In an alternative embodiment, the HMGB1 inhibitor may be a RNA molecule such as a siRNA, short hairpin RNA, microRNA, antisense RNA targeting the HMGB1 gene. In an embodiment, the RNA molecule is a siRNA. The RNA molecule may comprise or consist of a sequence of SEQ ID NO: 1 or SEQ ID NO: 2. The RNA molecule may be modified in accordance with practical need. Other suitable RNA molecules capable of targeting HMGB1 gene may also be used in the present invention.

The expression "effective amount" generally denotes an amount sufficient to produce therapeutically desirable results, wherein the exact nature of the result varies depending on the specific condition which is treated. The HMGB1 inhibitor of the present invention may be contained in a composition, in particular a pharmaceutical composition, in an effective amount, i.e. an amount suitable to treat or prevent the *C. difficile* infection or its associated symptom or inhibit the colonization, growth and/or proliferation of *C. difficile* in a subject, in particular a mammal, which also depends on the frequency and number of compositions to be administered. In an embodiment, the HMGB1 inhibitor of the present invention may be administered to a subject, particularly a mammal such as rodent, at a dosage of about 50 mg/kg or above. In other embodiment, the compound may be administered at a concentration of about 25 mg/kg, 50 mg/kg, 75 mg/kg or 100 mg/kg.

The term "subject" in particular refers to an animal or human, in particular a mammal and most preferably human. In an embodiment, the subject has a reduced expression of cytokine CCL2 particularly before administering the HMGB1 inhibitor compared to a healthy individual and/or before TcdB intoxication. The subject may also be a patient administered with an antibiotic before and has a low resistance against *C. difficile* bacterium.

In an embodiment where the subject is human, particularly an adult, the compound may be administered at a dosage of about 50 mg to 200 mg per day, about 75 mg to 150 mg per day, or about 80 to 120 mg per day.

When the compound is provided in a pharmaceutical composition to a subject, the skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

In embodiments of the present invention, the HMGB1 inhibitor as disclosed herein is administered to the subject by a route selected from a group consisting of oral delivery, intravenous delivery, intradermal delivery, intraperitoneal delivery and intramuscular delivery. In particular, the compound is administered to a subject via intraperitoneal delivery. The person skilled in the art is able to formulate the HMGB1 inhibitor in a pharmaceutical composition according to the target site in the body of the subject.

The present invention further provides a method of inhibiting toxin-induced cytotoxic effect in intestinal tissues or cells such as colon cells. In an embodiment, the method comprises the step of contacting the colon cells with an effective amount of a HMGB1 inhibitor.

In an embodiment, the intestinal tissues or cells particular colon cells are infected by *C. difficile*, and the cytotoxic effect is induced by *C. difficile* toxin B. The method may comprise a step of incubating the colon cells in a medium comprising the HMGB 1 inhibitor for a period of time for example for at least 6 h, at least 12 h, at least 18 h, or at least 24 h.

In an embodiment, the intestinal tissues or cells are susceptible to *C. difficile* infection. In particular, the intestinal tissues or cells may be subject to an antibiotic before contacting with the HMGB1 inhibitor.

Preferably, the HMGB1 inhibitor is as described above. In a particular embodiment, the HMGB1 inhibitor is glycyrrhizin or its derivative.

In a further aspect, the present invention relates to use of the HMGB1 inhibitor as described above in the treatment of *C. difficile* infection or its associated symptom, particularly *C. difficile* infection or its associated symptom induced by toxin B. Moreover, the present invention also relates to use of the HMGB1 inhibitor as described above in the preparation of a medicament for treating *C. difficile* infection or its associated symptom.

EXAMPLES

The inventors determined the host factors of TcdB via screenings and test, and unexpectedly found that HMGB1 has an important role in TcdB induced apoptosis and cell damage. Subsequently, a HMGB1 inhibitor was used to determine the efficacy of it on inhibitory cell death induced by TcdB. The experiments are described in detail below.

Production of TcdB Proteins

Recombinant TcdB proteins particularly from *C. difficile* strain 630 were produced in *Bacillus megaterium* cells and purified by Ni-NTA chromatography. FIG. 1A shows the SDS-PAGE gel pattern of recombinant TcdB protein obtained after purification. TcdB is the potential cause for apoptosis and cell death. To determine intoxicating dose and screening readout, the inventors performed cell viability and caspase-3&7 activity assays in Caco-2 cells in 96-well plate.

Caco-2 cells were cultured in Dulbecco's Modified Eagle's Medium (DMEM; Gibco #) supplemented with 10% fetal bovine serum (FBS, Gibico #) at 37° C. with 5% carbon dioxide.

After exposure to serial dilutions of TcdB, from 0.001 to 75 nM, cell viability was measured at 18 h post-intoxication using the CellTiter-Glo luminescent cell viability assay (G7572; Promega). Apoptosis was quantified by measuring caspase 3/7 activation in a luminescent signal using Caspase 3/7 Glo assay (G8092; Promega).

Figure 1B:
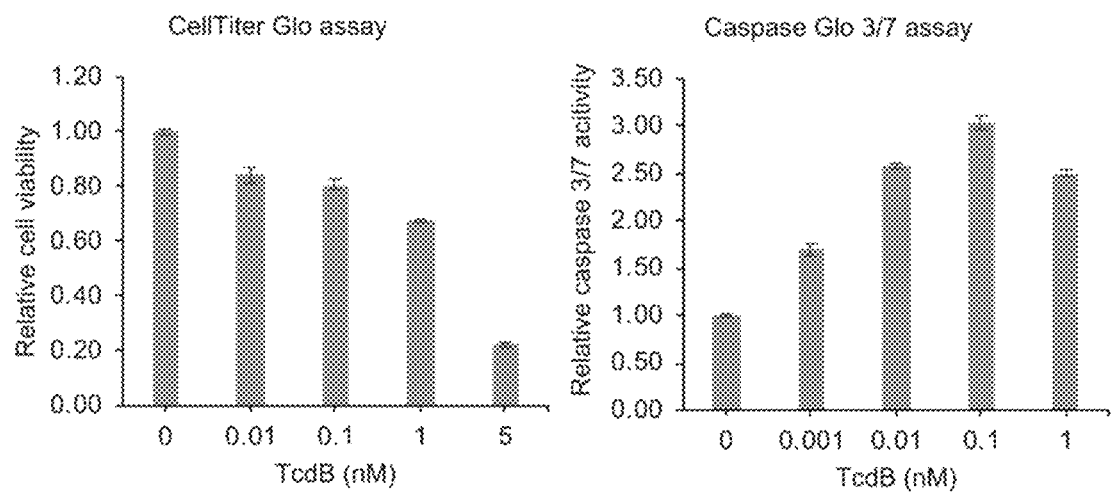

As shown in FIG. 1B, it demonstrated that TcdB, at 0.01 nM induced Caco-2 cell death compared to the control group, i.e. untreated cells, and the cell death rate was dose dependent from 0.01 to 5 nM of TcdB. In accordance with the Caspase-Glo 3/7 assay (Promega), which measures caspase 3/7 activity, there was significant caspase activation at 0.01 nM and 0.1 nM of TcdB.

Figure 1C:
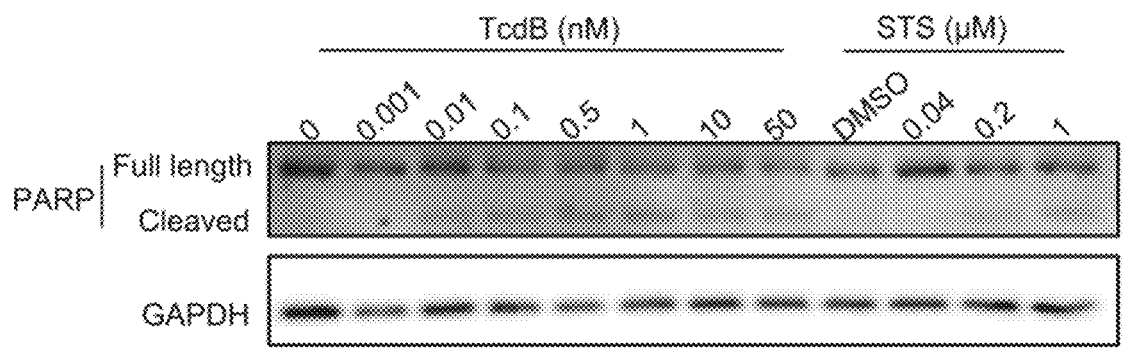

Western blotting assay was performed to determine the caspase cleavage of PARP. FIG. 1C confirmed that there was a caspase activation at 0.01 nM caused by TcdB. Staurosporine (STS) was used as the positive control in this assay.

Identification of Host Factors of TcdB

For screening host factors of TcdB, two positive controls using siRNA targeting p22phox and UDP-glucose pyrophosphorylase (UGP2) were included. p22phox, a component of NOX complex, its silencing has been confirmed to protect Caco-2 cells against TcdB induced cell death. UGP2 has been identified to be used by TcdA and TcdB to glucosylate GTPase. Therefore, to minimize the effect caused by these two components, Caco-2 cells were transfected with the respective siRNA targeting them for inhibiting their effects.

Figure 1D:
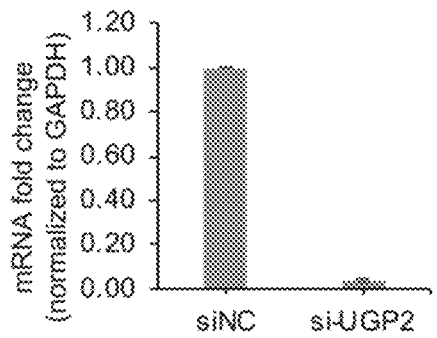
Figure 1D:
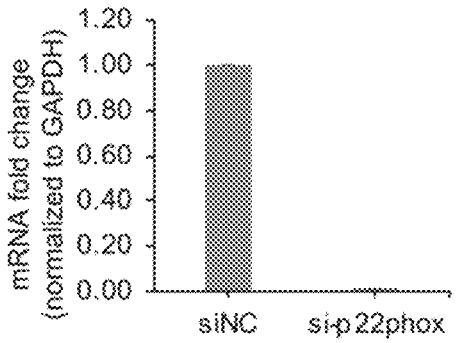
Figure 1E:
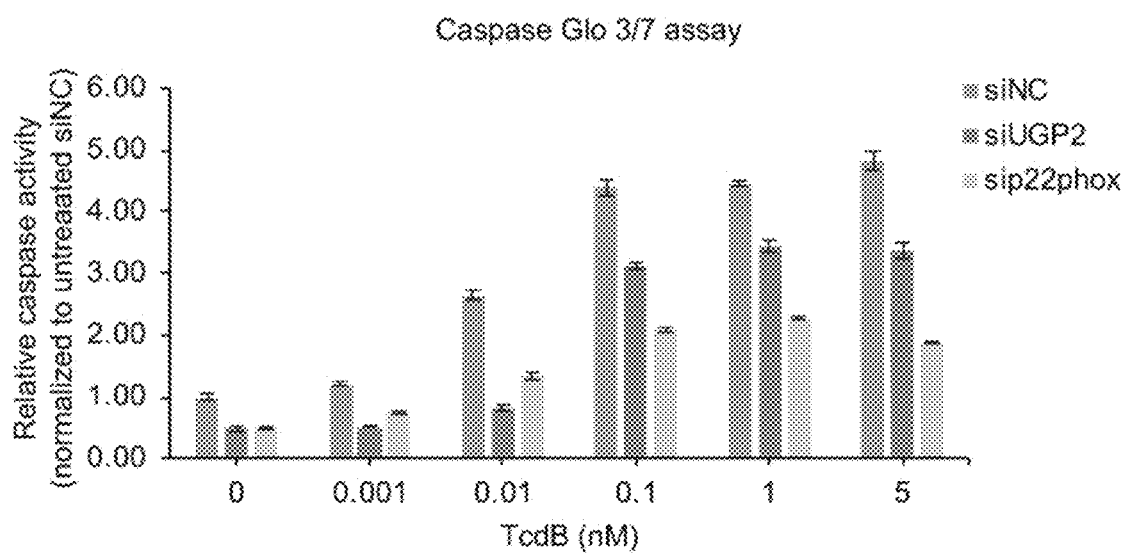

As shown in FIG. 1D, the two siRNAs in Caco-2 cells achieved 90% knockdown at mRNA level. Referring to FIG. 1E, in TcdB-treated cells, caspase 3/7 activity was significantly reduced in p22phox and UGP2 siRNA transfected cells compared with negative control siRNA (siNC) transfected cells.

siRNA transfection in the experiments was generally performed using a reverse-transfection approach. In brief, 0.5 µl chemically synthesized siRNA (10 µM stock) was diluted in 50 µl opti-MEM. RNAiMAX (Life Technologies) was prepared in 50 µl opti-MEM at 0.2 µl per well, mixed with diluted siRNA, and incubated at room temperature for 15 min before being added into a 96 well plate at 50 µl/well. Then 50 µl of $2\times10^4$ cells/mL was added into each well, followed by 48 h of incubation at 37° C. For each target, three wells received mock treatment and other wells challenged with different concentrations of TcdB for 18 h, triplicate for each concentration. Cell viability was determined with the CellTiter-Glo luminescent Cell viability assay. The average treated value was normalized to the average mock value to establish percent survival. Transfection efficiency was confirmed using qPCR.

Figure 2A:
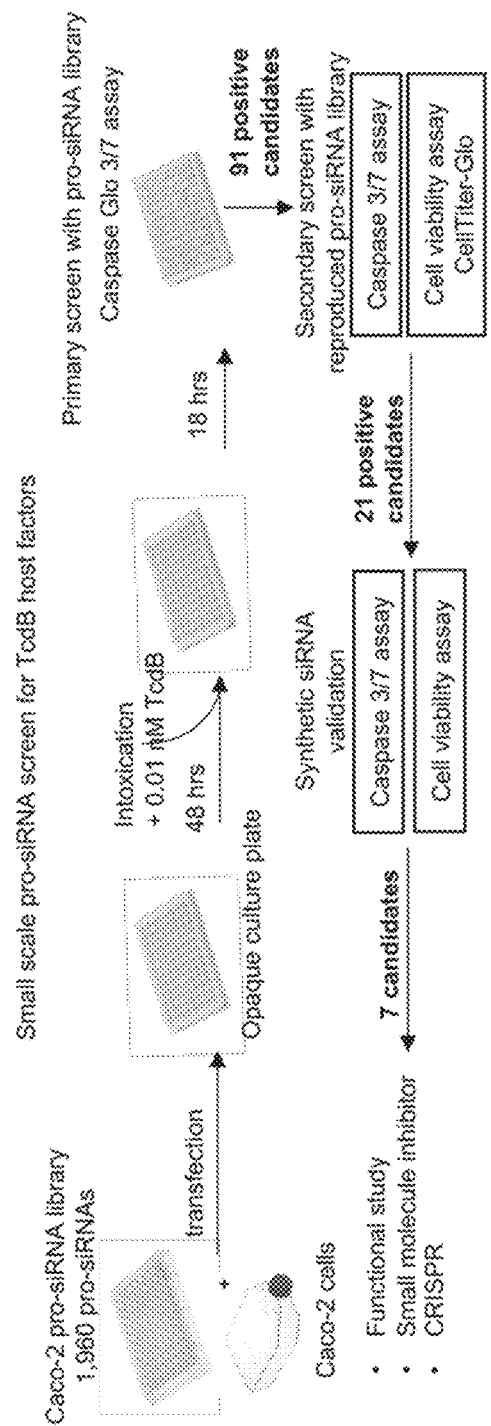

Then, to identify cellular factors involved in TcdB induced cell damage, the inventors produced a small scale of pro-siRNA library with around 2000 siRNAs specifically aimed for Caco-2 cells. Two rounds of screening were performed according to the scheme demonstrated in FIG. 2A. The details of the process are described below.

Before screening, the total RNA was extracted from Caco-2 cells and cloned into a vector pET28a. The pro-siRNA library plasmid contained a His-tagged p19 protein, which enabled the production and purification of siRNAs derived from bacteria, and a double-stranded RNA producing cassette, which enabled the generation of sequence specific siRNAs derived from the sequence inserted between the two opposing T7 promoters through the SacI site. Cloning of pro-siRNA plasmid library followed method used for making cDNA library as previously described. Each pro-siRNA clone produced a pro-siRNA targeting a random gene expressed in target cells. To produce a large number of individual pro-siRNAs covering all the expressed genes, the inventors devised a method for high-throughput bacterial culture and pro-siRNA purification in 96-well plates. Thousands of individual pro-siRNAs were purified using a high-throughput and automated method by KingFisher Flex Purification System (ThermoFisher).

Figure 2B:
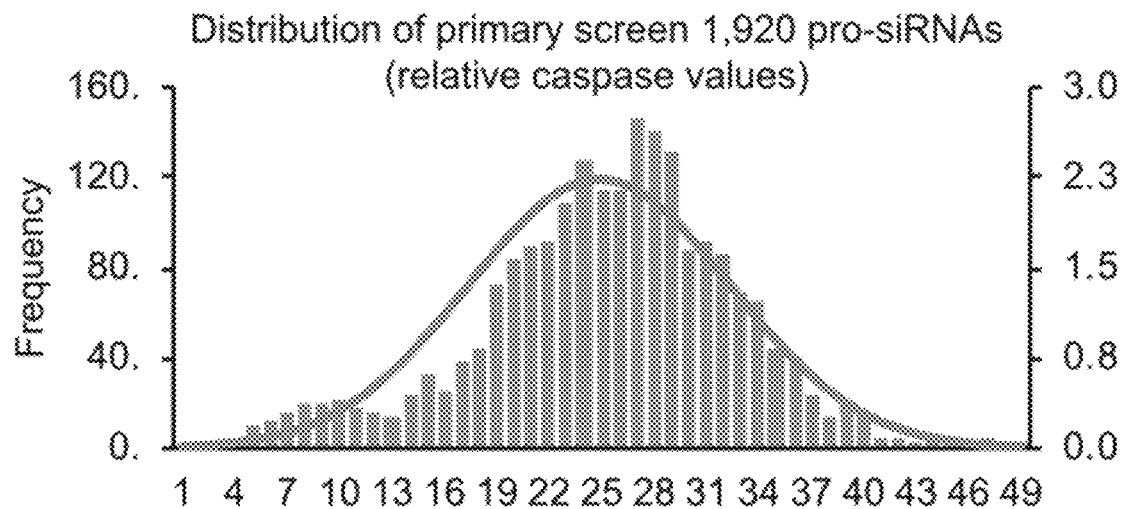
Figure 2C:
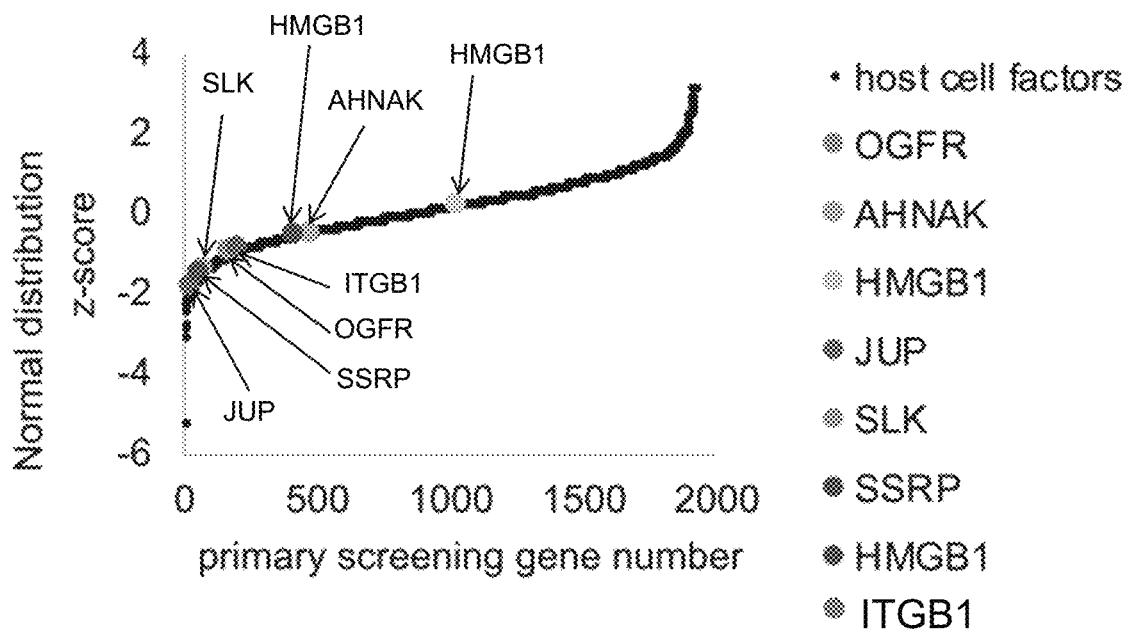
Figure 2D:
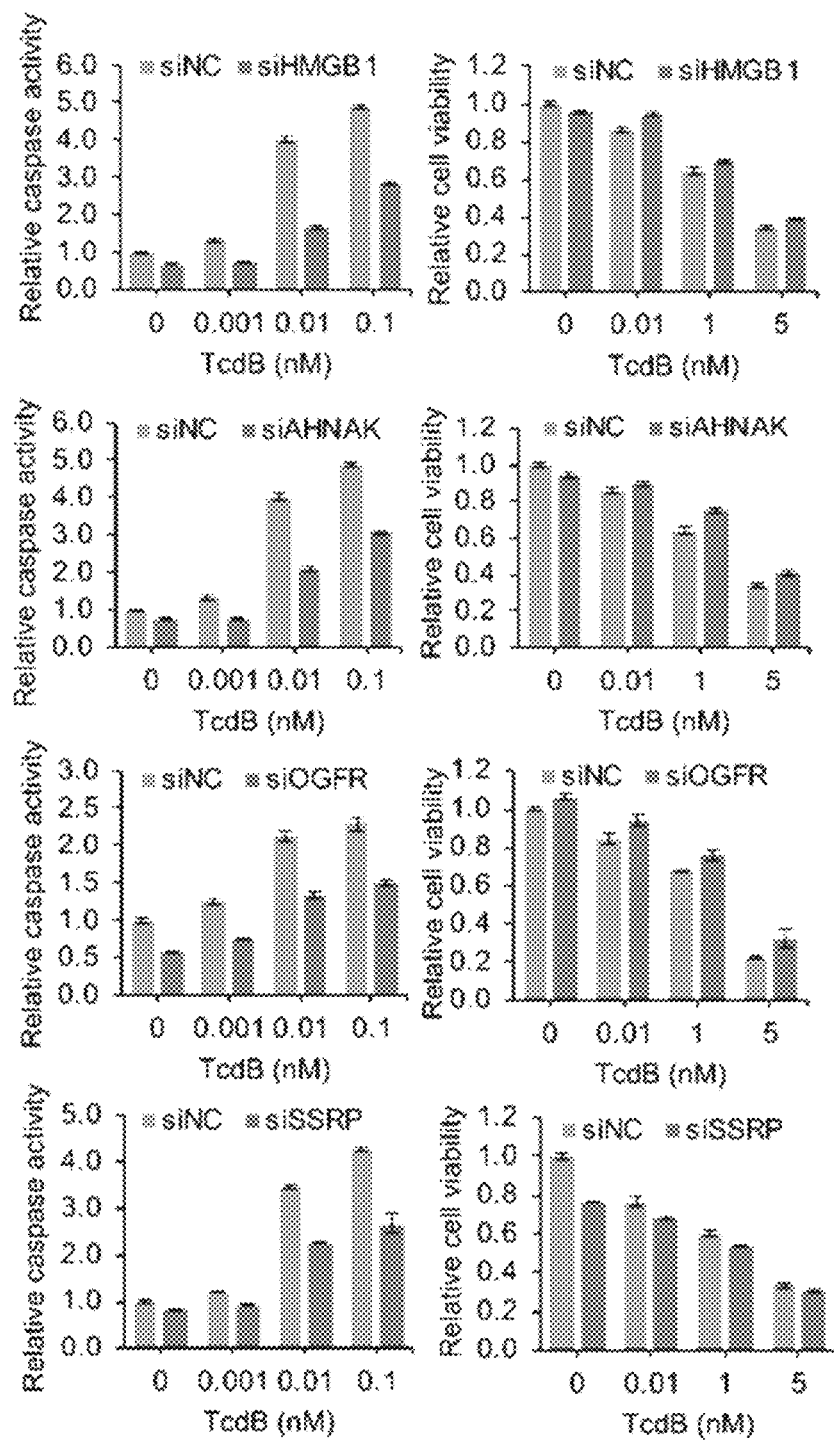
Figure 2E:
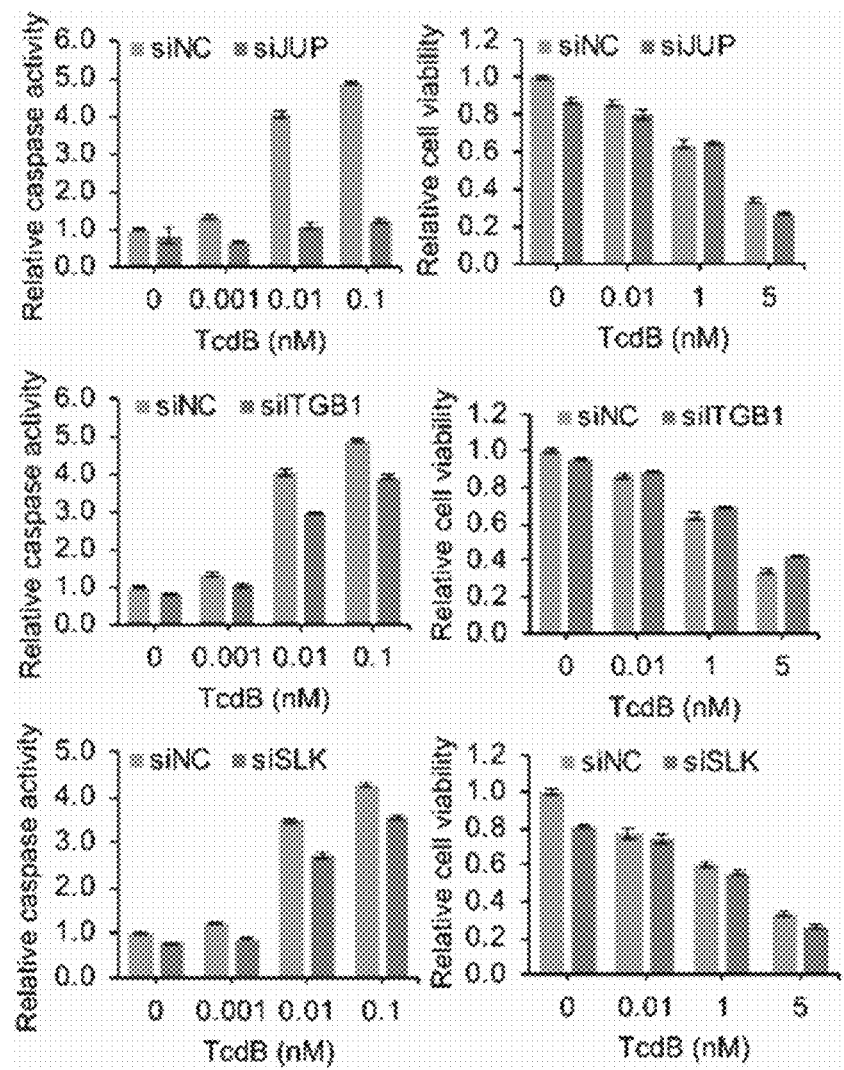

The inventors conducted two rounds of screening. A library of individual 2,000 siRNA targeting human genome was used in primary screening. For both the primary and second screens, Caco-2 cells were transfected with the pro-siRNA (100 nM) using the lipofectamine RNAiMAX. The transfected cells were incubated in DMEM supplemented with 10% FBS at 37° C. for 48 h, and then the library of cells was treated with 0.01 nM TcdB for 18 h. After 18 h, caspase activity was assayed using Caspase 3/7 Glo (Promega). In each 96-well plate, there were additional control wells with a non-targeting control siRNA for determining the general effect of siRNA transfection on intoxication, and siRNA targeting p22phox and UGP2, host genes known to be required for the intoxication of TcdB, whose silencing reduces the caspase activity for determining general knockdown efficiency. Based on the change of positive control, the inventors defined an apoptosis reduction of greater than Mean-STD after TcdB treatment 18 h as the threshold for hit selection. As shown in FIGS. 2B and 2C, data from primary screening show normal distribution, and selected candidates are located in the left edge, the region of lower caspase values. The Z' factor, which reflects the assay quality control of high content screening for Caco-2 cells was 0.716762. Since a Z' factor larger than 0.5 indicates a robust screening assay, the caspase assay in the system was suitable for high-throughput screening.

Figure 5A:
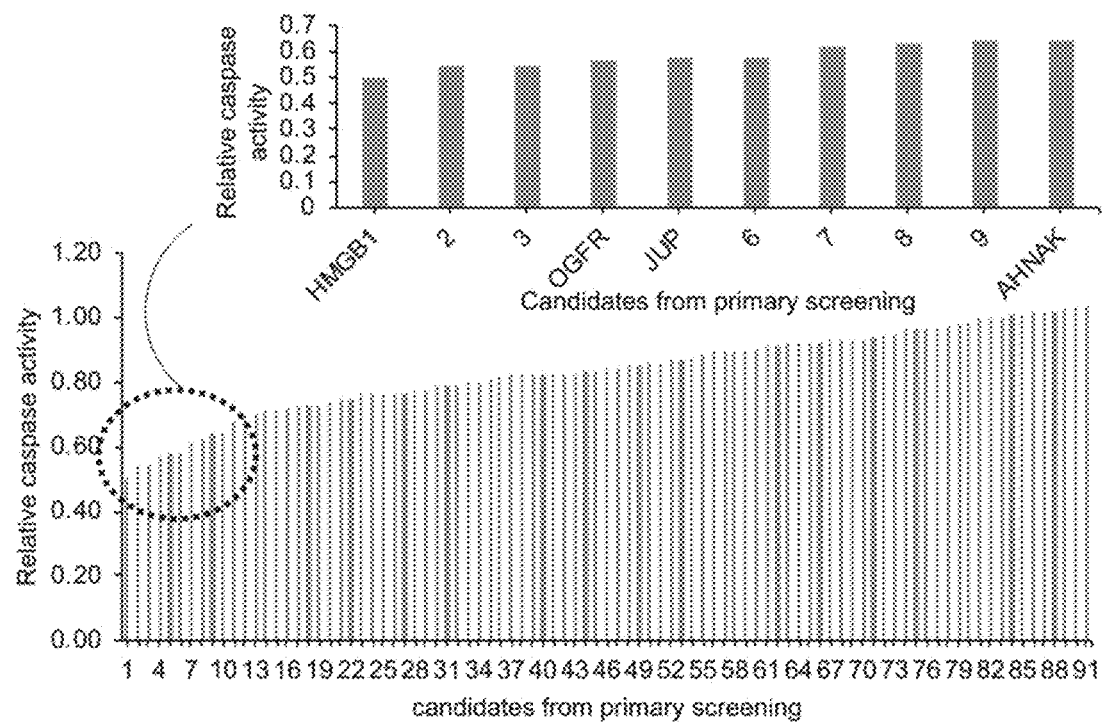
FIG. 5A shows the caspase activity of the 91 positive candidates identified by the primary screen and the relative caspase activity of 7 identified candidates.
Figure 5B:
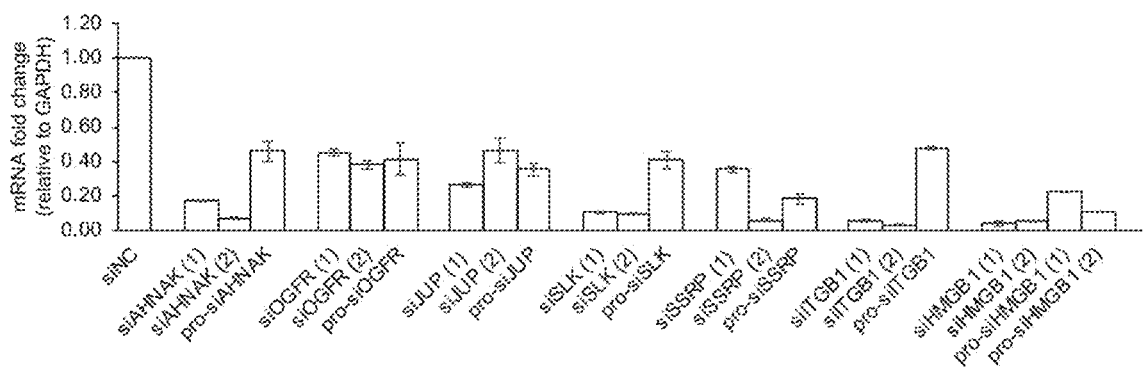
FIG. 5B is a plot demonstrating that mRNA expression of the candidate genes after knockdown, in which synthetic siRNAs were used and pro-siRNAs knockdown efficiency was determined by qRT-PCR.
Figure 6A:
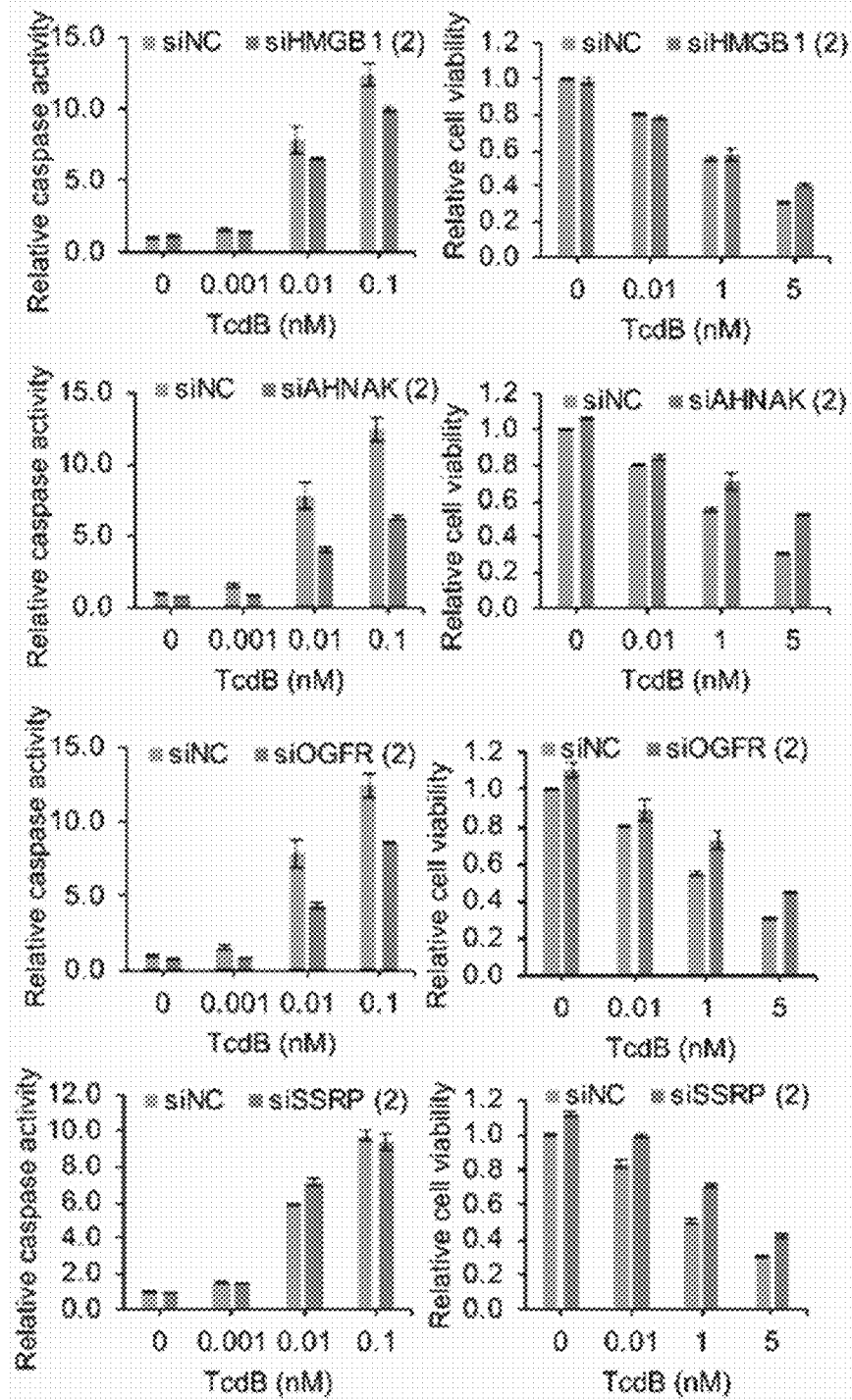
FIGS. 6A and 6B show the relative caspase activity and cell viability of Caco-2 cells transfected with corresponding siRNA targeting the 7 candidate genes including HMGB1, AHNAK, OGFR, SSRP, JUP, ITGB1 and SLK for validation. Data were collected from three independent replicates.
Figure 6B:
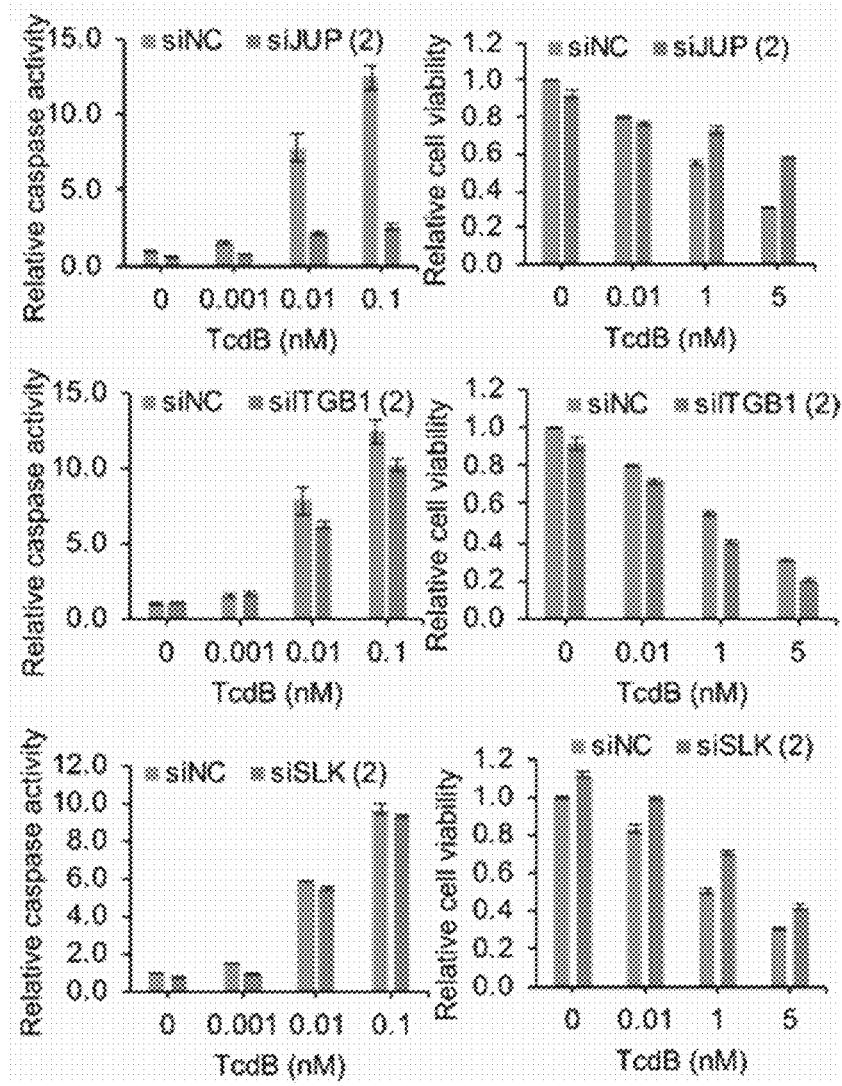

The inventors then determined whether siRNAs silencing affected cell viability, or helped toxin induce higher cell death rates. The inventors designed a second screening using caspase assay plus cell viability assay to weed out siRNAs with those activities. The activity of these primary hits from the caspase-3 activity assay were re-evaluated in TcdB-exposed Caco-2 cells, and, notably, was performed in parallel with the cytotoxicity assay. Cytotoxic siRNAs were then eliminated from the confirmed-hit list. With reference to FIGS. 2D, 2E, 6A and 6B, the inventors identified 7 candidates shown to reduce TcdB induced caspase activation and either increase or have no effect on cell viability. The 7 candidate genes identified are OGFR, AHNAK, HMGB1, JUP, SLK, SSRP, ITGB1. All 7 candidates decreased the apoptosis caused by TcdB at different level. For each of the candidate genes, the inventors designed 2 synthetic siRNAs and performed siRNA knockdown experiments to confirm the results obtained by pro-siRNA. However, only some of them could rescue cell viability, such as siRNAs targeting ITGB1, HMGB1, JUP, AHNAK and OGFR, and at different extent. qRT-PCR confirmed the knockdown efficiency of all two sets of siRNAs and pro-siRNAs from library targeting the genes (FIG. 5B).

As the top hit in the second screening (FIG. 5A), knockdown of HMGB1 gene expression rescued TcdB induced cell death and reduced caspase 3/7 activation, demonstrating the important role of HMGB1 in the interaction between TcdB and host cells.

Effect of Glycyrrhizin on TcdB-Induced Cell Damage or Death

Glycyrrhizin was used to determine whether it can prevent HMGB1-induced apoptosis. Briefly, Caco-2 cells were pretreated with 100 µM, 200 µM, 400 µM and 800 µM of chemical synthesized glycyrrhizin and two commercially compositions i.e. compound glycyrrhizin injection (denoted as CGI) and Magnesium Isoglycyrrhizinate Injection (denoted as MII), and then exposed to different concentrations of TcdB ranging from 0.001 nM to 5 nM. Glycyrrhizin Injection (CGI) was purchased from Minophagen Pharmaceutical Co. LTD (Japan). Magnesium Isoglycyrrhizinate (GM) injection was purchased from Chia Tai Tianqing Pharmaceutical Group Co., Ltd.

Figure 3A:
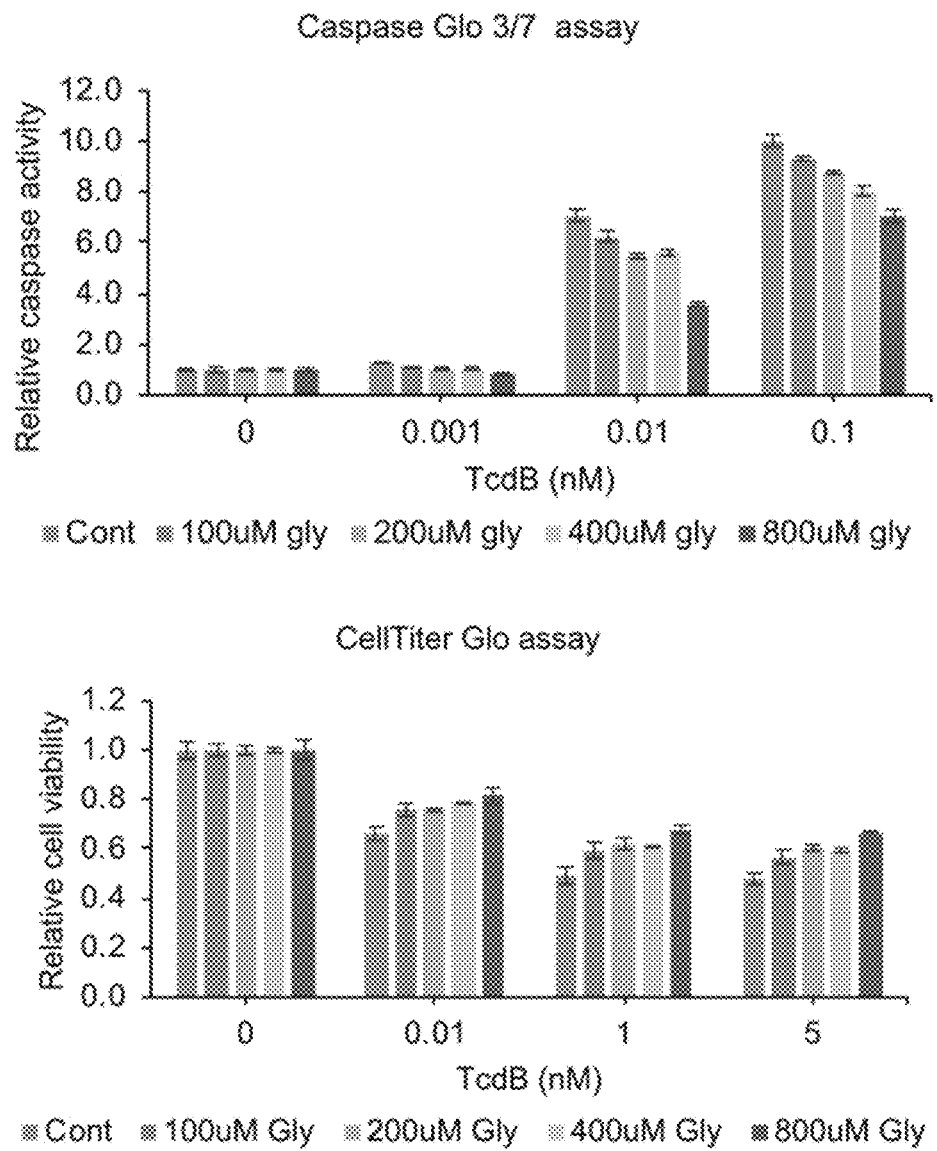
Figure 3B:
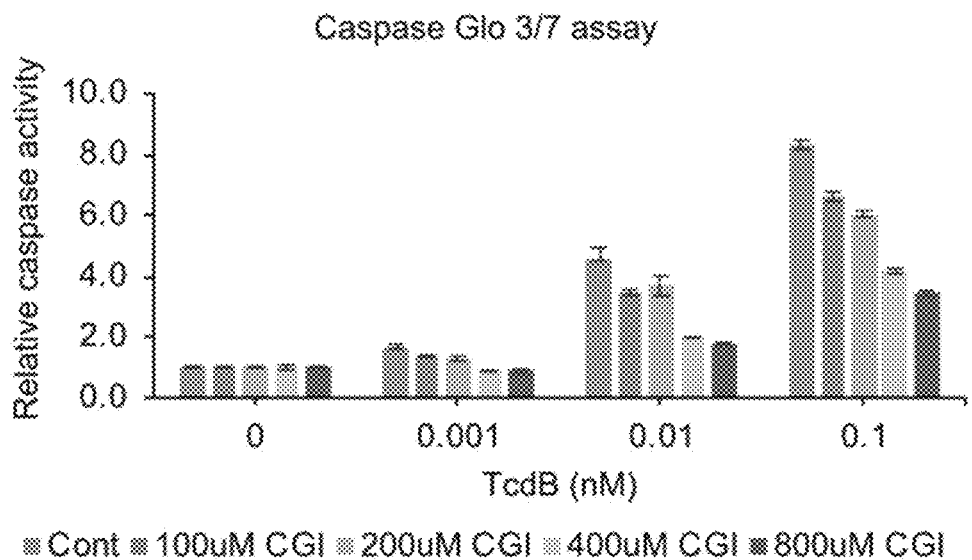
Figure 3B:
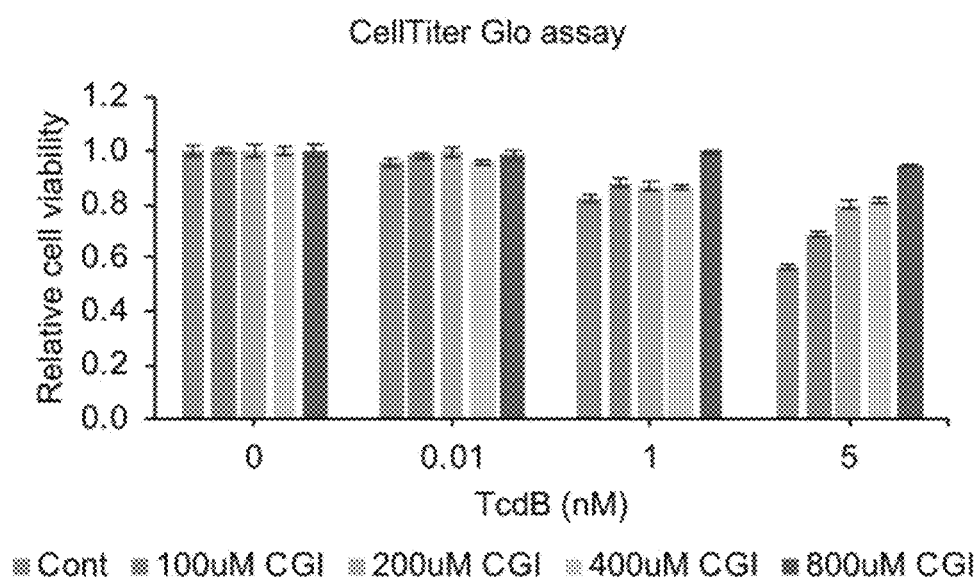
Figure 3C:
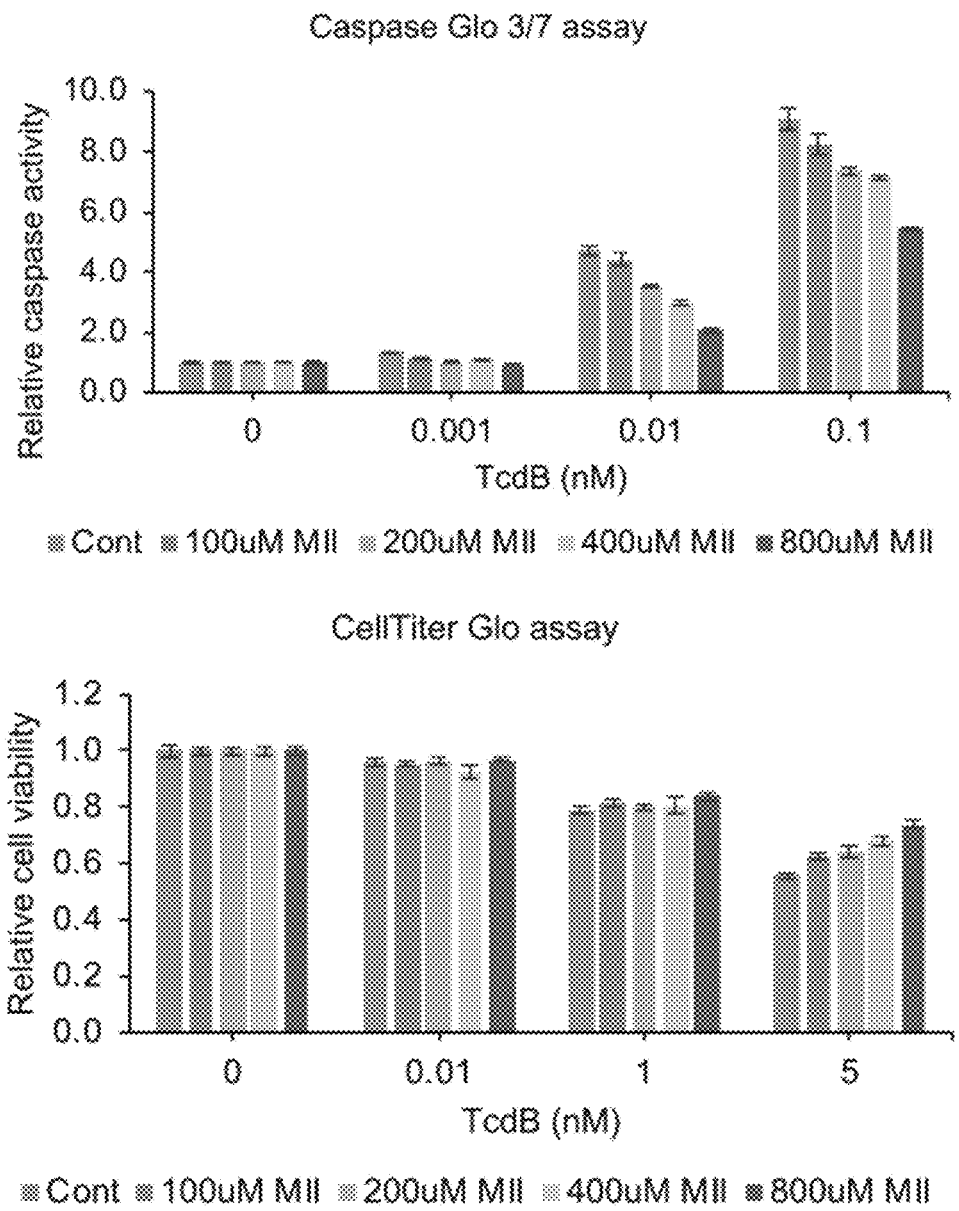

With reference to FIGS. 3A, 3B and 3C, it was found that both chemical and commercially available glycyrrhizin alleviated TcdB induced cytotoxicity and reduced caspase activation compared with groups pretreated with control buffer.

Figure 7A:
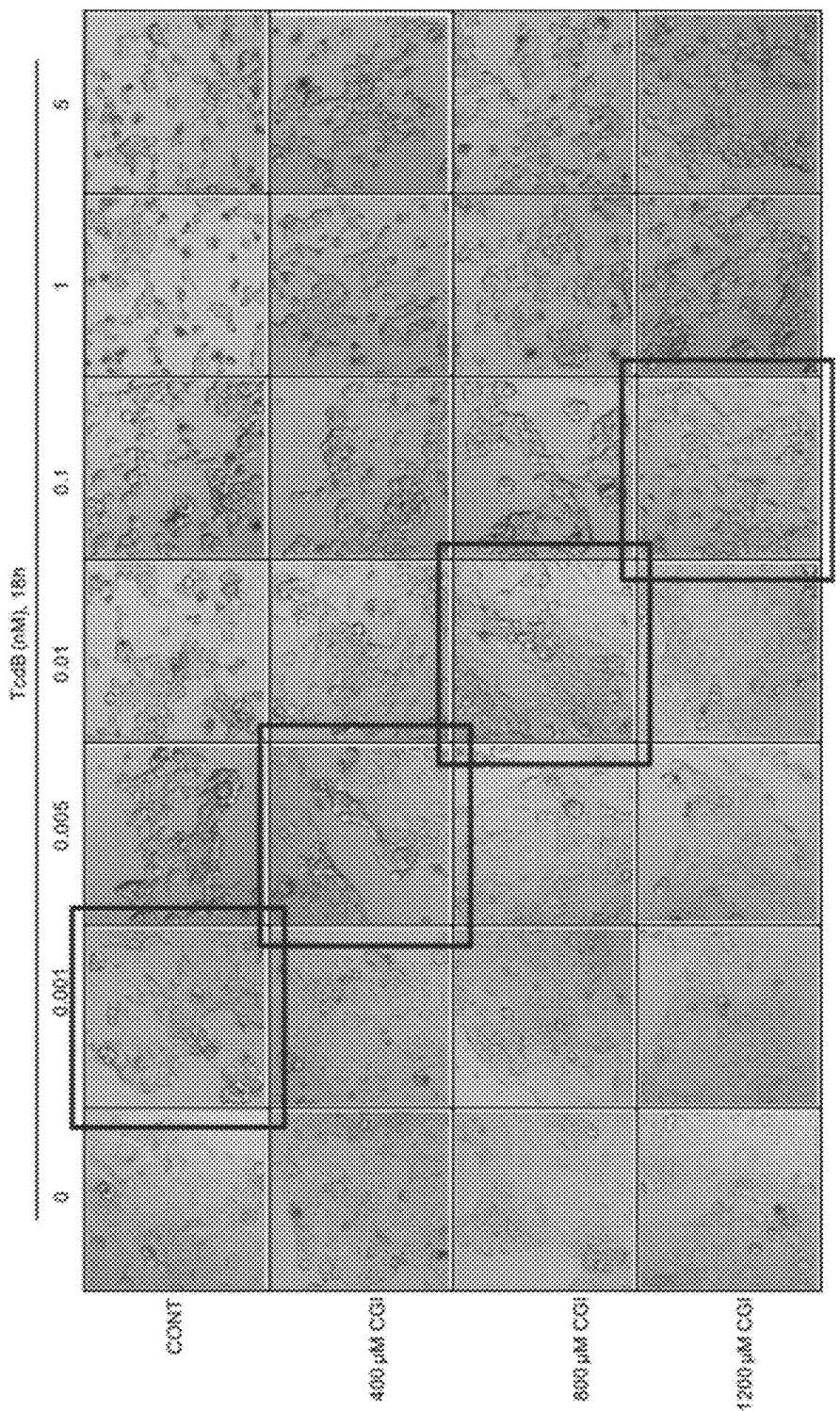
FIG. 7A shows microscopic images of Caco-2 cells after pre-treatment with different concentrations of CGI and followed by intoxication with a series of concentration of TcdB, wherein the images were capture after 18 h of intoxication and analyzed using CellInsight CX7 High-Content Screening (HCS) Platform (Thermo Fisher), ×10 objectives.
Figure 7B:
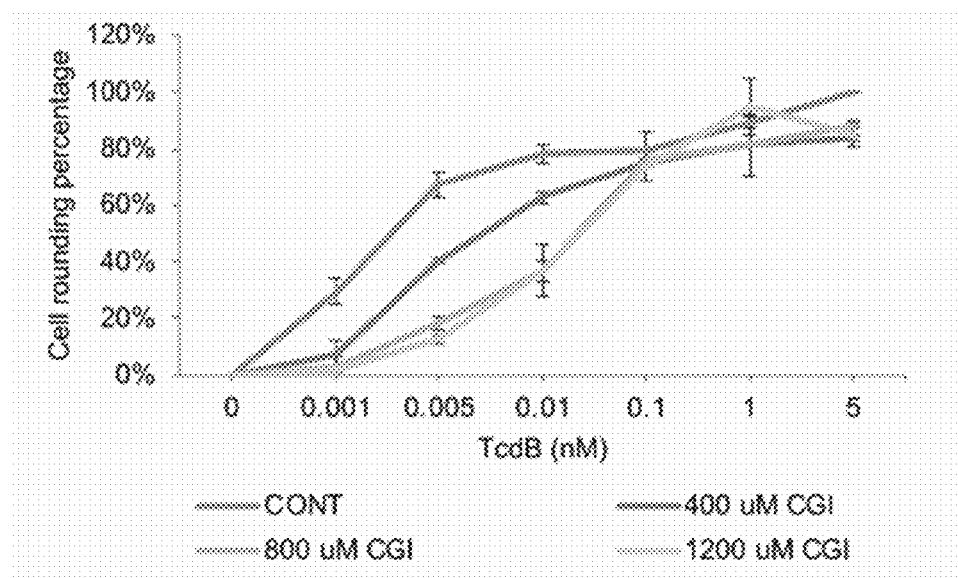
FIG. 7B is a plot showing of the cell rounding percentage of Caco-2 cells after pre-treatment with different concentrations of CGI and followed by intoxication with a series of concentration of TcdB for 18 h.

The inventors then determined the morphology changes of glycyrrhizin-pretreated cells. Cells pretreated with CGI showed increased resistance to TcdB induced cytopathic effects characterized by cell rounding in a dose dependent manner (FIGS. 7A and 7B) and the highest of CGI pretreatment group had around a 100-fold resistance to TcdB. The inventors found levels of cell rounding were positively correlated with nucleus intensity when stained with Hochest, so the inventors quantified cell rounding percentage based on Hochest stain intensity. With reference to FIG. 7B, the data showed that glycyrrhizin pretreatment delayed the onset of TcdB-induced cell rounding which is consistent with the images.

Figure 8:
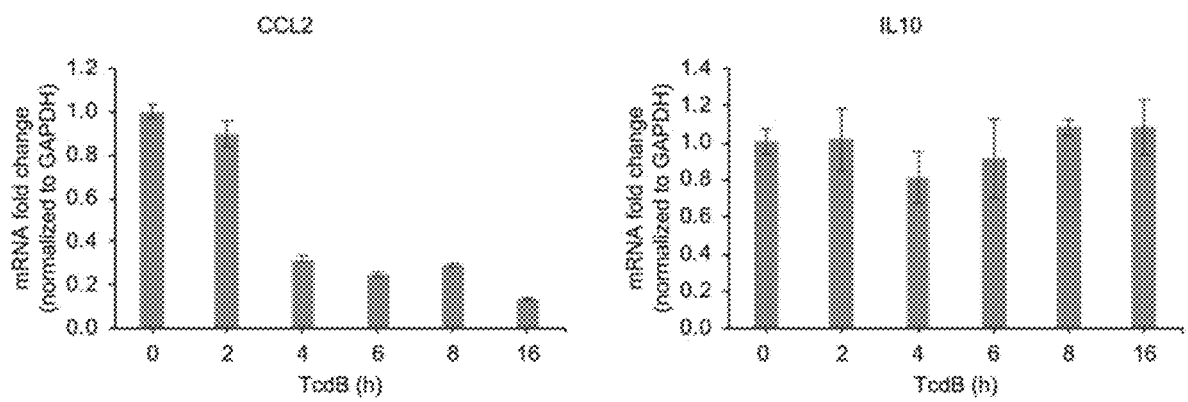
FIG. 8 shows the mRNA expression change of CCL2 and IL10 in Caco-2 cells after being exposed to 1 nM TcdB for different time periods, from 0 to 16 h.

There are studies suggesting that glycyrrhizin could enhance hosts immunity against infection by decreasing the expression of IL10 and CCL2 (MCP-1). To evaluate whether these cytokines are involved in tcdB induced apoptosis, the inventors detected the expression of these cytokines in treated cells under the previously described system. Results in FIG. 8 showed that CCL2 expression decreased after the cells being exposed to TcdB and IL10 had a very low expression level and no expression change after exposed to TcdB. Therefore, it was found that the protection of glycyrrhizin from TcdB is not done through regulating these cytokines. These data demonstrated the important role of HMGB1 in TcdB induced apoptosis in vitro and such an apoptosis can be alleviated by using a HMGB1 inhibitor for example glycyrrhizin.

The tests and evaluation were done by taking microscopic images using the CellInsight CX7 High Content Screening platform (Thermo fisher), and conducting qPCR, and immunoblot assay. Particularly, the total RNA was extracted from Caco-2 cells and reversed into cDNAs. qPCR was conducted with SYBR Green supermix (Bio-Rad). Immunoblotting was conducted by washing the treated cells twice with PBS and then collecting them with 1% SDS (plus 100 mM PMSF). The cell lysates were subject to SDS-PAGE and immunoblot analysis using antibody specifically against HMGB1.

The antibodies used in the experiments include: rabbit polyclonal antibody against PARP (CST, #9542), rabbit polyclonal antibody against HMGB1 (Abcam, ab18256); the HRP-conjugated goat anti-mouse IgG (H+L) and HRP-conjugated goat anti-rabbit IgG (H+L) secondary antibodies purchased from Invitrogen.

Protective Effect of Glycyrrhizin Against TcdB in Animal Model

The inventors used a mice colon ligation loop model to mimic *C. difficile* infection as TcdB is released into the lumen of the colon during *C. difficile* infection. All procedures were performed according to the animal protocol approved by the Cornell University IACUC (2017-0112). 6-8 weeks old of C57BL/6 mice were administrated with glycyrrhizin acid (50 mg/kg) daily via intraperitoneal injection two days before surgery. After overnight fasting, mice were anaesthetized and dissected via a midline laparotomy. A length of about 2 cm colon tissue was ligated and either saline or TcdB was injected into ligated loop for treatment. Mice were sutured and allowed to recover. After 8 hours, mice were euthanized and the ligated colon segments were excised and subjected to H&E staining. HE scoring was blindly assessed by a pathologist.

Figure 4A:
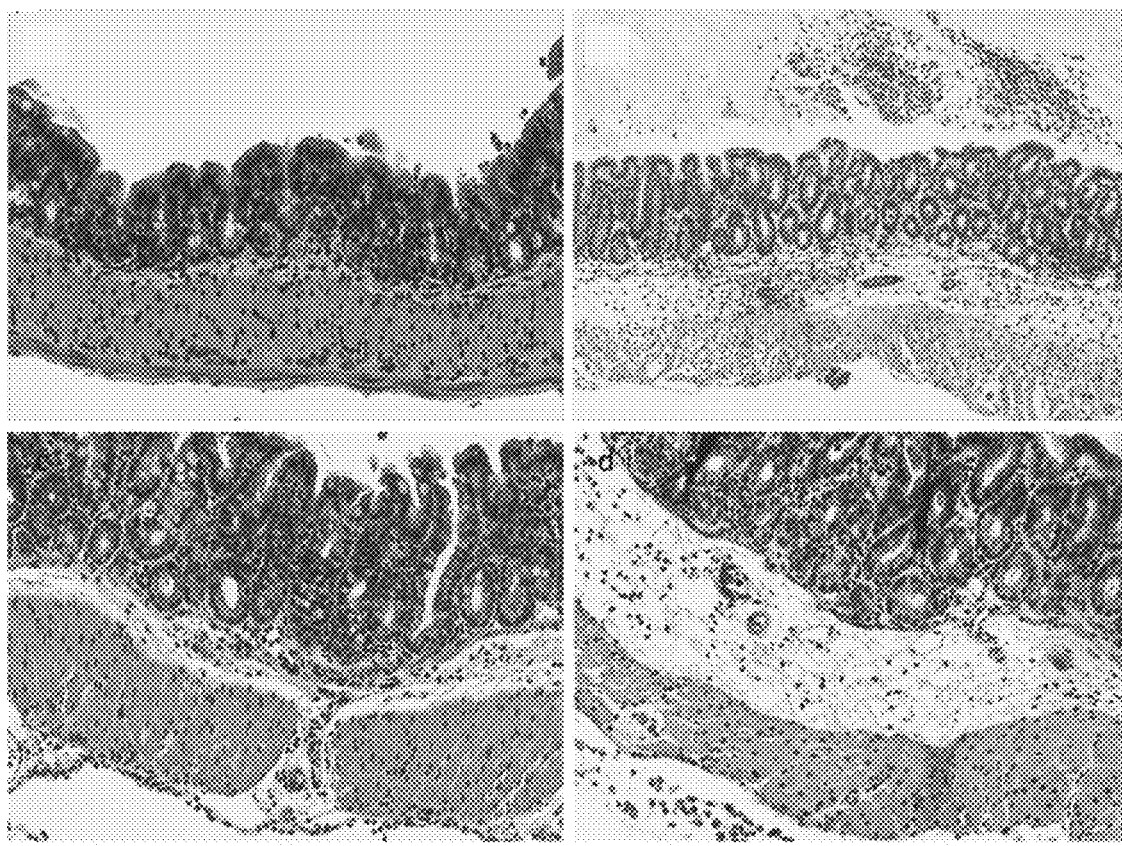
FIG. 4B is a plot showing the survival rate of mice treated with CGI on and after the day of *C. difficile* VPI 10463 spores challenge. Mice were monitored for the survival rate.
Figure 4A:
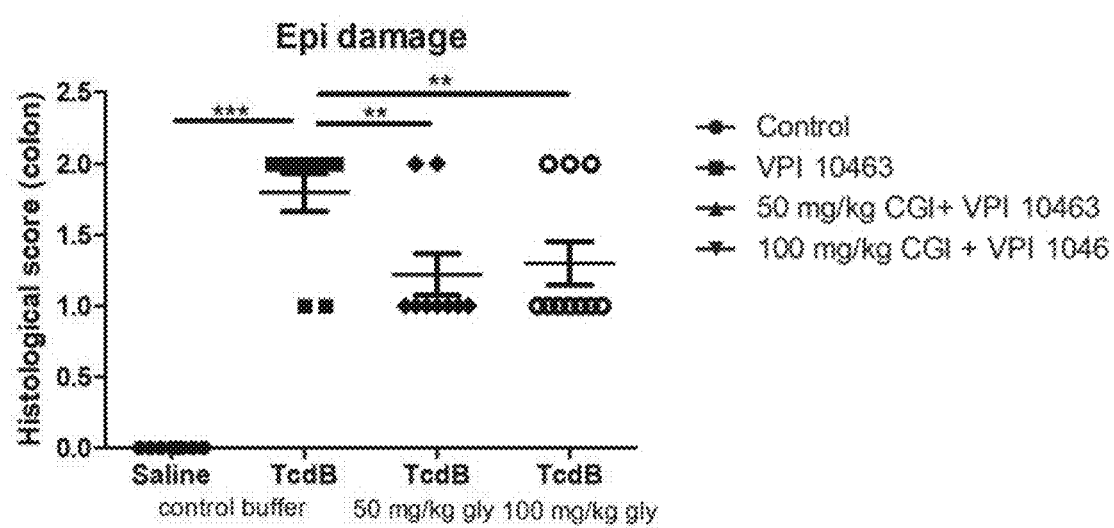

As shown in FIG. 4A, the histological scoring revealed that in the TcdB-treated control group, i.e. without glycyrrhizin pre-treatment, the ligated colon tissue had pseudomembrane formation in lumen, serious submucosa swelling, pervasive neutrophil infiltration and muscle vacuoles after 8 h of incubation with 10 μg TcdB. Glycyrrhizin pre-treatment groups have less epithelial layer damages. These data demonstrated that glycyrrhizin can exert protection against TcdB-induced disruption in colon epithelium and may be useful in inhibiting the HMGB1 activity induced by the TcdB. Accordingly, glycyrrhizin is capable of alleviating or minimizing the disorders caused by TcdB.

To further determine the in vivo protective effect of glycyrrhizin on mice, a *C. difficile* mice model was established particularly the one as described in Guo, S. et al, (2015), Vaccine 33, 1586-1595. Briefly, C57BL/6 mice were given water mixed with a mixture of kanamycin (Sigma, MO) ($0.4 \times 10^{-3}$ mg/L), gentamicin (Sigma, MO) ($0.035 \times 10^{-3}$ mg/L), colistin (Sigma, MO) (850 U/mL), metronidazole (Sigma, MO) ($0.215 \times 10^{-3}$ mg/L), and vancomycin (Sigma, MO) ($0.045 \times 10^{-3}$ mg/L) for 3 days. All mice were then provided with regular autoclaved water for 2 days and administered with a single dose of clindamycin (Sigma, MO) (10 mg/kg) intraperitoneally 1 day before the *C. difficile* challenge. Mice were injected with glycyrrhizin daily on or before the day of *C. difficile* VPI 10463 spores challenge. All mice were then challenged with $1 \times 10^5$ of prepared *C. difficile* (strain VPI10463) spores by gavage feeding. The mice were intensively monitored daily after challenge for the presence and severity of diarrhea and other symptoms of illness or mortality. Body weight was measured once a day at the same time each day. Mice judged to be in a moribund state were euthanized by carbon dioxide.

Figure 4B:
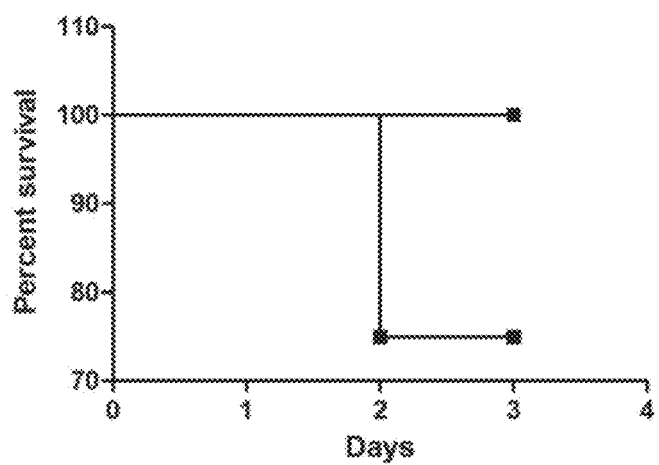

With reference to FIG. 4B, the survival rate showed that *C. difficile* VPI 10463 spores challenged groups had 75% survival while glycyrrhizin treated group had 100% survival at the end of experiment. Those data suggest that glycyrrhizin has protective effect against TcdB-induced cell death and particularly against *C. difficile* infection.

Conclusion

Based on the experiments conducted, the inventors found two TcdB resistant clones in the HMGB1 locus and were able to confirm the importance of HMGB1 in TcdB induced cytotoxicity. HMGB1 is a highly conserved protein that is normally localized in the nucleus of almost all eukaryotic cells to act as a nuclear cofactor in transcription regulation. In addition to its intracellular functions, HMGB1 can be released into extracellular environment by two distinct ways: secreted actively by living immune cells such as macrophages, or released passively by dead or dying cells. Extracellular HMGB1 can activate inflammatory responses and contribute to many inflammatory diseases by binding into cell specific receptors. HMGB1 and its B-box domain have been demonstrated to be capable of causing alterations in intestinal barrier function.

In the present invention, the inventors unexpectedly found that inhibition of HMGB1 gene expression can reduce TcdB induced caspase activation, indicating that HMGB1 is involved in the TcdB mediated apoptosis pathway. Therefore, a HMGB1 inhibitor such as a chemical compound, e.g. glycyrrhizin, and a small RNA molecule such as siRNA may be useful in treating *C. difficile* or its associated symptom. Glycyrrhizin is proven to be effective in curtailing TcdB induced cell death. For example, glycyrrhizin pretreatment can increase cell viability, decrease caspase activation, and enhance cell rounding resistance. In vivo results also demonstrated that glycyrrhizin has protection effect against TcdB induced epithelium damage possibly by neutralizing extracellular secreted HMGB1. Accordingly, a HMGB1 inhibitor particularly glycyrrhizin is useful in development of drugs for alleviating TcdB induced symptoms and treating *C. difficile* infection.

The invention claimed is:

1. A method of treating a subject suffering from *Clostridium difficile* infection or its associated symptom, comprising administering a therapeutic effective amount of a HMGB1 inhibitor to the subject, wherein the HMGB1 inhibitor is (a) glycyrrhizin or its derivative or (b) a small RNA molecule targeting HMGB1, wherein the sequence of the small RNA molecule is SEQ ID NO: 1 or SEQ ID NO: 2, and wherein the *C. difficile* infection is toxin B-induced *C. difficile* infection.

2. The method of claim 1, wherein the small RNA molecule is a siRNA.

3. The method of claim 1, wherein the HMGB1 inhibitor is administered to the subject by a route selected from a group consisting of oral delivery, intravenous delivery, intradermal delivery, intraperitoneal delivery and intramuscular delivery.

4. The method of claim 1, wherein the administration of the HMGB1 inhibitor delays or inhibits the onset of TcdB induced tissue damage in the subject.

5. The method of claim 1, wherein the subject has a reduced expression of CCL2 before administering the HMGB1 inhibitor compared to a healthy individual.

* * * * *